United States Patent [19]

Coates et al.

[11] 4,011,321

[45] Mar. 8, 1977

[54] PHARMACEUTICAL COMPOSITIONS AND METHODS OF INHIBITING β-ADRENERGIC RECEPTORS

[75] Inventors: William John Coates, Welwyn Garden City; Anthony Maitland Roe, Hatfield; Robert Antony Slater, Letchworth, all of England

[73] Assignee: Smith Kline & French Laboratories Limited, Welwyn Garden City, England

[22] Filed: Sept. 15, 1975

[21] Appl. No.: 613,601

Related U.S. Application Data

[62] Division of Ser. No. 531,957, Dec. 12, 1974, Pat. No. 3,931,177.

[52] U.S. Cl. .......................... 424/250; 424/248.56; 424/248.54
[51] Int. Cl.² ...................................... A61K 31/495
[58] Field of Search ........................... 424/250, 248

[56] References Cited

UNITED STATES PATENTS 3,689,652  9/1972  Curran et al. .................. 260/250 A

FOREIGN PATENTS OR APPLICATIONS 779,390  8/1972  Belgium ........................ 260/250 A

*Primary Examiner*—Albert T. Meyers
*Assistant Examiner*—Daren M. Stephens
*Attorney, Agent, or Firm*—Joan S. Keps; Richard D. Foggio; William H. Edgerton

[57] ABSTRACT

The compounds are 6-(3-substituted amino-2-hydroxy-propoxyaryl)-4,5-dihydro-3(2H)-pyridazinones which are β-adrenergic blocking agents.

11 Claims, No Drawings

PHARMACEUTICAL COMPOSITIONS AND METHODS OF INHIBITING β-ADRENERGIC RECEPTORS

This is a division of application Ser. No. 531,957 filed Dec. 12, 1974, now U.S. Pat. No. 3,931,177.

This invention relates to pharmacologically active compounds and in particular to certain substituted aryl dihydro pyridazinones which are active as β-adrenergic blocking agents and some of which (see below) also have acute antihypertensive activity. It also relates to pharmaceutical compositions comprising them and to methods of treatment employing their use.

The compounds of the present invention may be represented by the following Formula I:

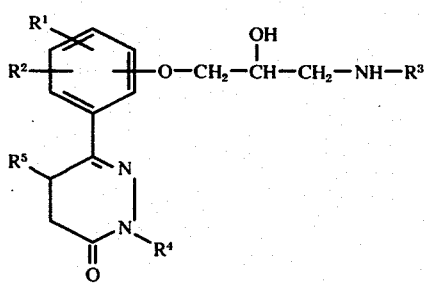

FORMULA I wherein $R^1$ is hydrogen, lower alkyl, lower alkenyl, —$CF_3$, halogen, cyano, nitro, hydroxy, lower alkoxy, lower alkenyloxy, amino, lower alkanoylamino, lower alkylamino, di lower alkylamino or morpholino:

$R^2$ is hydrogen, methyl or, together with $R^1$, forms a benzene ring fused to the benzene ring shown to form a naphthyl group;

$R^3$ is isopropyl or tertiary butyl; and $R^4$ and $R^5$, which may be the same or different, are hydrogen or methyl. This invention also includes pharmaceutically acceptable acid addition salts of the compounds of Formula I.

Throughout the present specification and claims, by the terms "lower alkyl," "lower alkenyl," "lower alkoxy" and "lower alkenyloxy" we mean alkyl, alkenyl, alkoxy and alkenyloxy groups containing a chain of no more than four carbon atoms, which chain may, where possible, be branched.

Preferably $R^1$ is hydrogen, methyl, allyl, chloro, cyano, nitro, lower alkoxy, allyloxy, acetylamino or morpholino and $R^2$ is hydrogen.

The compounds of the present invention wherein $R^1$ is methyl, acetylamino, cyano or nitro, particularly acetylamino, cyano and nitro and $R^2$ is hydrogen possess acute antihypertensive activity in addition to β-adrenergic blocking activity. This group of compounds are referred to hereinafter as the AAH group. When both activities are required the AAH group is therefore particularly preferred.

The relative position of the pyridazine ring and the 3-alkylamino-2-hydroxy-1-propoxy side chain has been found to have an effect on the activity of the compounds, and we therefore prefer compounds of Formula I wherein:

a. the 3-alkylamino-2-hydroxy-1-propoxy side chain is ortho to the pyridazine ring and $R^1$ and $R^2$ are hydrogen, e.g., 6-[2-(3-t-butylamino-2-hydroxypropoxy)-phenyl]-4,5-dihydro-3(2H)-pyridazinone.

b. the 3-alkylamino-2-hydroxy-1-propoxy side chain is ortho to the pyridazine ring and $R^1$ is other than hydrogen and is meta or para to the 3-alkylamino-2-hydroxy-1-propoxy side chain, e.g., 6-[5-acetylamino-2-(3-t-butylamino-2-hydroxypropoxy)phenyl]-4,5-dihydro-3(2H)-pyridazinone.

c. the 3-alkylamino-2-hydroxy-1-propoxy side chain is meta or para to the pyridazine ring and $R^1$ is other than hydrogen and is ortho to the 3-alkylamino-2-hydroxy-1-propoxy side chain. e.g., 6-[3-allyl-4-(2-hydroxy-3-isopropylaminopropoxy)-phenyl]-4,5-dihydro-3(2H)-pyridazinone and 6-[3-(3-t-butylamino-2-hydroxypropoxy)-4-methylphenyl]-4,5-dihydro-3(2H)-pyridazinone.

d. (when $R^1$ is acetylamino, $R^2$ is hydrogen and acute antihypertensive properties are required) the pyridazine ring, the 3-alkylamino-2-hydroxy-1-propoxy side chain and $R^1$ respectively are in a 1,2,4- or 1,2,5- arrangement e.g., 6-[5acetylamino-2-(3-t-butylamino-2-hydroxypropoxy)phenyl]-4,5-dihydro-3(2H)-pyridazinone.

The compounds of Formula I may be produced from intermediate compounds of the following Formula II:

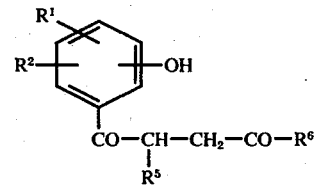

FORMULA II wherein $R^1$, $R^2$ and $R^5$ have the same significance as in Formula I and $R^6$ is hydroxy, amino or any other suitable group such as lower alkoxy or lower alkylamino. As mentioned hereinafter $R^1$ may also be protected or a precursor of those groups set out in Formula I. The compounds of Formula II may be produced from the corresponding phenols of Formula III:

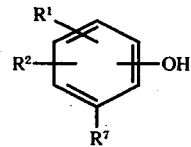

FORMULA III wherein $R^1$ and $R^2$ have the same significance as in Formula I and $R^7$ is hydrogen, bromine or $COCH_2R^5$. When $R^7$ is hydrogen, reaction with succinic anhydride and a Lewis acid such as aluminium trichloride may be used. When $R^7$ is bromine, formation of a Grignard reagent with magnesium and subsequent reaction of this with, for example N-methylsuccinimide provides a useful method, the phenolic group being protected during this reaction for example by benzylation. In either case of course the succinic anhydride of N-methylsuccinimide may be substituted with a methyl group to give the appropriate compounds of Formula II wherein $R^5$ is methyl. An alternative method for preparing compounds of Formula II wherein $R^5$ is methyl is to treat a compound of Formula III wherein $R^7$ is hydrogen with citraconic anhydride and reduce the product with zinc and acetic acid.

When $R^7$ is $-COCH_2R^5$, the phenol of Formula III is treated with formaldehyde and a di-lower alkyl amine to give a compound of Formula IV wherein $R^8$ is lower alkyl or $(R^8)_2$ is a polymethylene chain which forms a heterocyclic ring with the nitrogen atom shown. The compounds of Formula IV may be alkylated to give the corresponding quaternary derivatives. The compounds of Formula IV and the corresponding quaternary derivatives may be treated with an inorganic cyanide to give a cyanide of Formula V. The phenol group may be protected, for example as the acetate ester, during these processes.

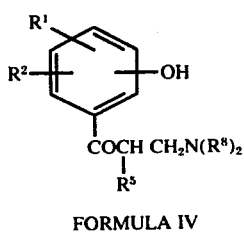

FORMULA IV

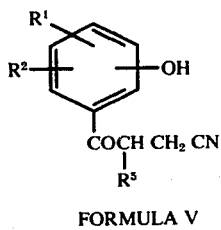

FORMULA V

The compounds of Formula II may readily be obtained from the cyanides of Formula V e.g., by hydrolysis of the latter to the corresponding amides or carboxylic acids.

Treatment of the compounds of Formula II with hydrazine or methylhydrazine leads to the formation of compounds of Formula VI (see scheme 1) wherein $R^1$, $R^2$, $R^4$ and $R^5$ have the same significance as in Formula I and subsequent reaction first with epichlorohydrin or epibromohydrin (to give the compound of Formula VII) and then with an amine of Formula $R^3 NH_2$ wherein $R^3$ has the same significance as in Formula I leads to the required products of the present invention. As shown in the attached reaction scheme it is also possible first to attach the 3-alkylamino-2-hydroxy-1-propoxy side chain and then to form the pyridazine ring (i.e. via the compounds of Formulae VIII and IX) and this route is preferred when the hydroxyl group in Formula II is ortho to the $COCHR^5CH_2COR^6$ group. When using this route it is preferred that $R^6$ be alkoxy and epibromohydrin is used.

It will be understood that $R^1$ where appropriate e.g., when it is a substituent other than hydrogen which might be affected by the conditions of any of the various reaction stages described above in going from the compound of Formula III to that of Formula I, may be suitably protected or may exist as a precursor to the required group. For example, when $R^1$ in Formula I is to be amino or substituted amino, $R^1$ in Formula III and II may be nitro, the required amino compound being formed by reduction after the final stage of the reaction scheme shown. It is also of course possible in many cases to introduce such a group or its precursor as the final stage of the synthesis.

As stated above, the compounds of Formula I are β-adrenergic blocking agents and the AAH group are also acute antihypertensive agents. β-Adrenergic blocking agents are useful in the treatment of angina pectoris, cardiac arrhythmias and hypertension. It will be appreciated that the AAH group of the present invention which cause a fall in blood pressure without tachycardia are particularly useful.

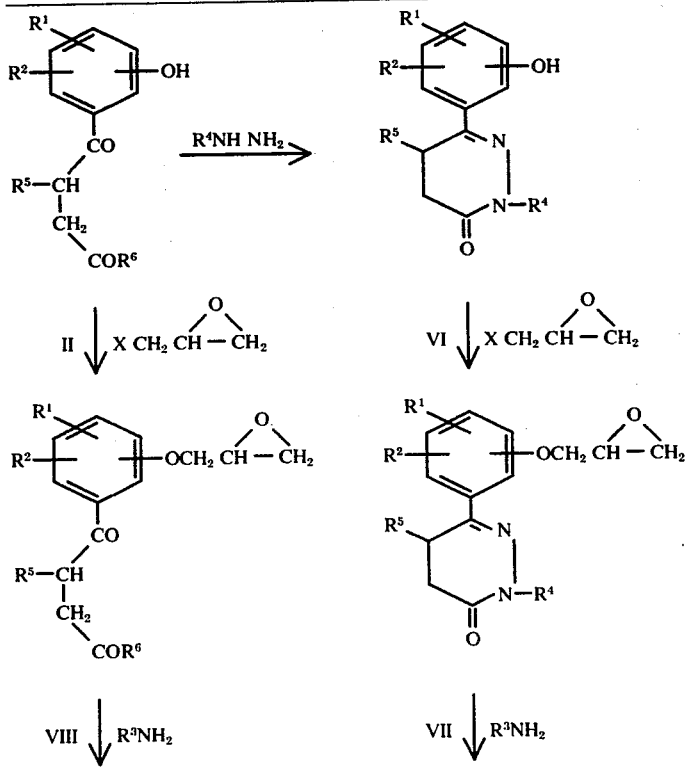

-continued
SCHEME 1

(X represents Cl or Br)

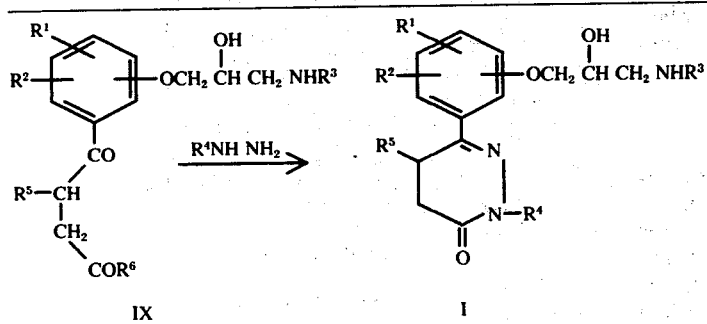

IX → I

The β-adrenergic blocking activity of our compounds may be demonstrated in a suitable test preparation such as cats anaesthetised with pentobarbitone sodium (Nembutal), 60mg/Kg i.p. In such anaesthetised cats, intravenous injections of isoprenaline cause tachycardia and vasodilatation in the hind-limb. These effects of isoprenaline, which are dose-dependent and are due to stimulation of β-adrenoreceptors can be reduced or abolished by intravenous administration of from 0.01 to 100 micromoles/Kg of the β-adrenergic blocking agent of Formula I.

The acute antihypertensive activity of our compounds may be demonstrated in a suitable test preparation such as rats of a spontaneously hypertensive strain. Our compounds are subcutaneously or orally administered at a dose of from 0.1 to 1000 micromoles/Kg to these rats and the blood pressure and heart rate are monitored directly, from indwelling polythene cannulae placed in the carotid artery, over a period of 6 hours commencing one hour before the administration of the compound.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric, acetic, citric and maleic acids.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25mg to about 500mg. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to produce β-adrenergic blockade and, where applicable, lowering of blood pressure. The route of administration may be orally or parenterally.

Preferably, each dosage unit will contain the active ingredient in an amount of from about 25mg to about 500 mg most preferably from about 50 mg to about 250 mg.

The active ingredient will preferably be administered in equal doses one to three times per day. The daily dosage regimen will preferably be from about 100 mg to about 2g.

Other pharmacologically active compounds may in certain cases be included in the composition. Advantageously the composition will be made up in a dosage unit form appropriate to the desired mode of administration, for example, as a tablet, capsule or injectable solution.

The invention is illustrated but in no way limited by the following examples:

EXAMPLE 1

Preparation of 6-[4-(2-Hydroxy-3-isopropylaminopropoxy)-phenyl]4,5-dihydro-3(2H)pyridazinone a. i. A solution of 4-benzyloxyphenyl magnesium bromide in tetrahydrofuran, prepared from 4-benzyloxybromobenzene (115g, 0.44 mole) and magnesium (20 g. 0.82 mole), was added during one hour to a well stirred, cooled solution of N-methylsuccinimide (74 g, 0.66 mole) in benzene (750 ml.). The reaction mixture was stirred overnight at room temperature, cooled with ice and hydrolysed with aqueous ammonium chloride (540 ml.). The aqueous phase was extracted with dichloromethane, and the combined organic solutions were washed with water, dried and evaporated to a slurry. Ether was added and the 2-(4-benzyloxyphenyl)-2-hydroxy--N-methyl-5-pyrrolidone (72.5g, 56.5%) was filtered off. The product, recrystallised from chloroform/methanol, had m.p. 105°–108° C.

(Found: C, 72.75; H, 6.39; N, 4.63. $C_{18}H_{19}NO_3$ requires: C, 72.71; H, 6.44; H, 4.71%).

2-(4-Benzyloxyphenyl)-2-hydroxy-N-methyl-5-pyrrolidone (50 g., 0.17 mole) was dissolved in hydrogen bromide in acetic acid (33%, 275 ml), the stirred solution was heated under reflux for three minutes and then allowed to cool. 2-(4Hydroxyphenyl)-N-methyl-2-pyrrolin-5-one hydrobromide (40 g, 88%, m.p. 223°–228° C) was collected and added in one portion to water (1 l.) and well stirred for 30 minutes. 3-(4-Hydroxybenzoyl)-N-methylpropionamide was collected, washed with water, and recrystallised from aqueous ethanol (26.6 g, 76%) m.p. 177°–179° C.

(Found: C, 63.57; H, 6.26; N, 6.69; M$^+$, 207. $C_{11}H_{13}NO_3$ requires: C, 63.75; H, 6.33; N, 6.76%; M, 207).

ii. A mixture of finely ground 3-(4-hydroxybenzoyl)-N-methylpropionamide (20.7 g, 0.1 mole), epichlorohydrin (77 g, 0.83 mole), and piperidine (0.5 ml) was heated on a steam bath for 90 minutes. Evaporation under reduced pressure gave a viscous oil which was dissolved in dichloromethane (500 ml) and shaken with dilute sodium hydroxide (100 ml). The organic phase was washed with water, dried and evaporated to a slurry. Addition of ether gave the required 3-[4-(2,3-epoxypropoxy)benzoyl]-N-methylpropionamide (21.36g.,81%) which was recrystallised from chloroform/ether, m.p. 133°–140° C.

(Found: C, 63.65; H, 6.58; N, 5.26; M$^+$, 263. $C_{14}H_{17}NO_4$ requires: C, 63.87; H, 6.51; N, 5.23%, M, 263).

iii. A mixture of 3-[4-(2,3-epoxypropoxy)benzoyl]-N-methylpropionamide (20 g, 0.076 mole), methanol (200 ml) and isopropylamine (36 ml, 0.42 mole) was heated under reflux for one hour. Evaporation under reduced pressure gave 3-[4-(2-hydroxy-3-isopropylaminopropoxy)benzoyl]-N-methylpropionamide (24 g, 97%, m.p. 139°–142° C). Crystallisation from water gave the pure amide, m.p. 140°–142° C.

(Found: C, 63.61; H, 8.31; N, 8.74; M$^+$, 322. $C_{17}H_{26}N_2O_4$ requires: C, 63.33; H, 8.13; N, 8.69%, M, 322).

iv. 3-[4-(2-Hydroxy-3-isopropylaminopropoxy)benzoyl]-N-methylpropionamide (5g, 0.015 mole) in 50% aqueous acetic acid (50 ml) was treated with hydrazine hydrate (2.4 ml, 0.047 mole) and heated under reflux for one hour. After evaporation under reduced pressure, the residue was dissolved in water, neutralised with aqueous sodium bicarbonate and extracted with dichloromethane. Evaporation of the dried organic solution gave 6-[4-(2-hydroxy-3-isopropylaminopropoxy)phenyl]-4,5-dihydro-3(2H)-pyridazinone (2.4 g, 50%, m.p. 108°–115° C). Crystallisation from water gave the pure pyridazinone, m.p. 116.5°–118° C.

(Found: C, 61.85; H, 7.42; N, 13.42; M$^+$, 305. $C_{16}H_{23}N_3O_3$ requires: C,. 62.92; H, 7.59; N, 13.76%, M,305).

b. i. A mixture of 6-(4-hydroxyphenyl)-4,5-dihydro3(2H)-pyridazinone (39.8g, 0.21 mole), epichlorohydrin (160 ml, 2.0 mole), and piperidine (0.9 ml) was stirred on a steam bath for 4 hours by which time the solid had dissolved. The solution was evaporated under reduced pressure to an oil which was dissolved in dichloromethane and shaken with dilute sodium hydroxide (150 ml) and with water. The dried solution was evaporated and treated with ethanol. 6-[4-(2,3-Epoxypropoxy)phenyl]-4,5-dihydro-3(2H)pyridazinone (38.5 g, 75%, m.p. 156°–158° C) was collected and recrystallised from ethanol, m.p. 157°–159° C.

(Found: C, 62.89; H, 5.72; N, 11.30. $C_{13}H_{14}N_2O_3$ requires: C, 63.39; H, 5.73; N, 11.38%).

ii. A mixture of the 6-[4-(2,3-epoxypropoxy)phenyl]-4,5dihydro-3(2H)-pyridazinone (38.37 g, 0.156 mole), isopropylamine (80 ml, 0.94 mole), and methanol (380 ml) was stirred under reflux for one hour, and then evaporated under reduced pressure to give 6-[4-(2-hydroxy-3-isopropylaminopropoxy)-phenyl]-4,5-dihydro-3(2H)-pyridazinone (47.59 g, 100%), m.p. 108°–113° C. The hydrochloride, crystallised from a mixture of 2-propanol, ethanol and ether, had m.p. 195°–200° C.

(Found: C, 56.15; H, 7.15; Cl. 10.28; N, 12.01; M$^+$, 305.$C_{16}H_{24}ClN_3O_3$ requires: C, 56.22; H, 7.08; Cl,10.37, N, 12.29;M(base)305).

EXAMPLE 2

Preparation of
6-[2-(2-Hydroxy-3-isopropylaminopropoxy)-phenyl]4,5-dihydro-3(2H)-pyridazinone i. Hydrogen chloride was bubbled into a gently boiling solution of the known 3-(2-hydroxybenzoyl)propionic acid (10 g, 0.05 mole) in dry methanol (20 ml) until esterification was complete. The solution was poured into ice-water and the ester extracted into dichloromethane. The organic solution was washed with water and evaporated to give methyl 3-(2-hydroxybenzoyl)propionate (10.55 g, 98%) as a pale yellow oil.

ii. A well stirred mixture of methyl 3-(2-hydroxybenzoyl)-propionate (63.3 g, 0.3 mole), potassium carbonate (48.4 g, 0.35 mole). epibromohydrin (117 ml, 1.4 mole), and dry ethyl methyl ketone (2000 ml) was heated under reflux for 28 hours. Evaporation of the filtered solution under reduced pressure gave methyl 3-[2-(2,3-epoxypropoxy)benzoyl]propionate (83 g, 100%).

(Found: M$^+$, 264. $C_{14}H_{16}O_5$ requires: M, 264).

iii. A stirred mixture of methyl 3-[2-(2,3-epoxypropoxy) benzoyl]-propionate (8.3g, 0.031 mole), methanol (85 ml), and isopropylamine (16.4 ml, 0.19 mole) was heated under reflux for 90 minutes. Evaporation of the solution under reduced pressure gave methyl 3-[2-(2-hydroxy-3-isopropylaminopropoxy)-benzoyl]propionate (10.2 g, 100%)as a pale brown oil.

iv. Hydrazine hydrate (4.65 ml, 0.09 mole) was added to a solution of methyl 3-[2-(2-hydroxy-3-isopropylaminopropoxy) benzoyl]propionate (10 g, 0.03 mole) in glacial acetic acid (80 ml) and the solution was heated under reflux for one hour. Evaporation under reduced pressure gave an oil (25.5 g.) which was dissolved in water, treated with an excess of sodium carbonate solution and extracted with dichloromethane. Evaporation of the dried extracts gave an oil (10.3 g.) which was purified on a silica column by elution with a mixture of chloroform and methanol to give 6-[2-(2-hydroxy-3-isopropyl-aminopropoxy)-phenyl]-4,5-dihydro-3(2H)-pyridazinone (6.25 g, 66%), m.p. 124°–126° C. The hydrochloride, crystallised from 2-propanol, had m.p. 162°–164.5° C.

(Found: C, 55.95; H, 7.19; Cl, 10.28; N, 12.09; M$^+$, 305.

$C_{16}H_{24}ClN_3O_3$ requires: C, 56.22; H, 7.08; Cl, 10.37; N, 12.29; M(Base)305).

EXAMPLE 3

Preparation of
6-[2-(3-t-Butylamino-2-hydroxypropoxy)phenyl]4,5-dihydro-3(2H)-pyridazinone.

i. A stirred mixture of methyl 3-[2-(2,3-epoxypropoxy)benzoyl]propionate (54.75 g, 0.21 mole) prepared according to Example 2(ii), methanol (580 ml) and t-butylamine (140 ml, 1.31 mole) was heated under reflux for 70 minutes. Evaporation of the solution under reduced pressure gave an oil (73 g) which crystallised when allowed to stand. Purification on a silica column by elution with mixtures of chloroform and methanol gave methyl 3-[2-(3-t-butylamino-2-hydroxypropoxy) benzoyl]propionate (55.4 g, 80%) which when recrystallised from benzene - petroluem ether (b.p. 60°-80° C) had m.p. 80°-81.5° C.

(Found: C, 63.63; H, 7.99; N, 3.90; M$^+$, 337. $C_{18}H_{27}NO_5$ requires: C, 64.09; H, 8.07; N, 4.15; M, 337).

ii. Hydrazine hydrate (22 ml, 0.44 mole) was added to a stirred solution of methyl 3-[2-(3-t-butylamino-2-hydroxypropoxy)benzoyl]propionate (48.8 g, 0.14 mole) in glacial acetic acid (500 ml) and the solution was heated under reflux for 90 minutes. Evaporation under reduced pressure gave an oil (127 g.) which was dissolved in water, treated with an excess of sodium carbonate solution and extracted with dichloromethane. Evaporation of the dried extracts gave an oil (49 g) which was purified on a silica column by elution with mixtures of chloroform and methanol to give 6-[2-(3-t-butylamino-2-hydroxypropoxy)phenyl]-4,5-dihydro-3(2H) pyridazinone (33.44 g, 72%, m.p. 138°-141° C.). The hydrochloride, crystallised from ethanol-ether, had m.p. 201°-203° C.

(Found: C, 57.18; H, 7.41; Cl, 9.67; N, 11.39; M$^+$, 319.

$C_{17}H_{25}N_3O_3$ . HCl requires: C, 57.36; H, 7.36; Cl, 9.96; N, 11.81;
M(Base), 319).

EXAMPLE 4

Preparation of
6-[2-(2-Hydroxy-3-isopropylaminopropoxy)phenyl]-2methyl-4,5-dihydro-3(2H)-pyridazinone i. Methylhydrazine (1 ml, 0.02 mole) was added to a stirred suspension of 3-(2-hydroxybenzoyl)propionic acid (2g, 0.01 mole) in water (20 ml). The resulting solution was heated under reflux for a few minutes and then allowed to cool. After the addition of water (20 ml), the 6-(2-hydroxyphenyl)-2-methyl-4,5-dihydro-3(2H)-pyridazinone (1.94 g, 92.5%, m.p. 139.5°-140.4° C) was collected and recrystallised from methanol, m.p. 140°-141° C.

(Found: C, 65.02; H, 5.96; N, 13.79; M$^+$, 204. $C_{11}H_{12}N_2O_2$ requires: C, 64.70; H, 5.93; N, 13.72%, M, 204).

ii. A mixture of 6-[2-(2,3-epoxypropoxy)phenyl]-2-methyl-4,5-dihydro-3(2H)-pyridazinone (1.05 g, 0.004 mole; prepared from the corresponding phenol by the method of Example 1 (b)(i), methanol (15 ml) and isopropylamine (2.1 ml, 0.024 mole) was heated under reflux for 90 minutes. The solution was evaporated under reduced pressure to give a viscous oil (1.43 g.), which was purified on a silica column by elution with a mixture of chloroform and methanol to give 6-[2-(2-hydroxy-3-isopropylaminopropoxy)phenyl]-2-methyl-4,5-dihydro-3(2H)-pyridazinone (0.97 g, 75%, m.p. 82°-84° C). The hydrochloride crystallised from 2-propanol, had m.p. 170°-171° C.

(Found: C, 57.62; H, 7.33; Cl, 9.73; N, 11.71; M$^+$, 319.

$C_{17}H_{26}ClN_3O_3$ requires: C, 57.36; H, 7.37; Cl, 9.94; N, 11.80%; M(base)319).

EXAMPLE 5

Preparation of
6-[4-(2-Hydroxy-3-isopropylaminopropoxy)-1naphthyl]-4,5-dihydro-3(2H)-pyridazinone i. A stirred suspension of 3-(4-hydroxy-1-naphthoyl)-propionic acid (80 g, 0.33 mole) in water (400 ml) was treated with hydrazine hydrate (24.6 ml, 0.49 mole) and heated under reflux for one hour. The cooled mixture was filtered, the product was washed with water and dried to give 6-(4-hydroxy-1-naphthyl)-4,5-dihydro-3(2H)-pyradazinone (66.05 g, 84%, m.p. 252°-258° C). Crystallisation from aqueous ethanol gave the pure pyridazinone m.p. 254°-258° C.

(Found: C, 69.97; H, 5.16; N, 11.41. $C_{14}H_{12}N_2O_2$ requires: C, 69.99; H, 5.03; N, 11.66%).

ii. A mixture of 6-(4-hydroxy-1-naphthyl)-4,5-dihydro-3(2H)-pyridazinone (0.5 g, 0.002 mole), epichlorohydrin (2g, 0.02 mole), and piperidine (0.02 g) was heated on a steam bath for 1.5 hours. Evaporation under reduced pressure gave an oil which was dissolved in dichloromethane and shaken with dilute sodium hydroxide (5 ml). The organic phase was washed with water, dried and evaporated to an oil which with ethanol-ether gave crystalline 6[4-(2,3-epoxy-propoxy)-1-naphthyl]-4,5-dihydro-3(2H)-pyridazinone (0.425 g, 69%, m.p. 151°-155° C). Crystallisation from ethanol gave the pure epoxide, m.p. 153.5°-155.5° C.

Found: C, 69.29; H, 5.44; N, 9.35. $C_{17}H_{16}N_2O_3$ requires: C, 68.90; H, 5.44; N, 9.45%).

iii. A mixture of 6-[4-( 2,3-epoxypropoxy)-1-naphthyl]-4,5-dihydro-3(2H)-pyridazinone (10 g, 0.034 mole), methanol (100 ml) and isopropylamine (17.4 ml, 0.2 mole) was heated under reflux for one hour. Evaporation under reduced pressure gave an oil which was purified on a silica column with chloroform-methanol to give 6-[4-(2-hydroxy-3-isopropylaminopropoxy)-1-naphthyl]-4,5-dihydro-3(2H)-pyridazinone (9g, 75%, m.p. 131°-135° C.). The hydrochloride, crystallised from 2-propanol had m.p. 195°-197° C.

(Found: C, 61.12; H, 6.55; Cl, 8.93; N, 10.58; $C_{20}H_{26}ClN_3O_3$ requires: C, 61.30; H, 6.66; Cl, 9.05; N, 10.72.).

EXAMPLE 6

Preparation of
6-[4-Allyl-3-(2-hydroxy-3-isopropylaminopropoxy)-phenyl-4,5-dihydro-3(2H )-pyridazinone a. i. Hydrogen chloride was bubbled into a gently boiling solution of 3-(3-hydroxybenzoyl)propionic acid (40 g, 0.21 mole) in dry methanol (80 ml) until esterification was complete. The solution was poured into ice-water (700 ml) and the product extracted into ether. The combined ethereal solutions were washed in turn with water and sodium bicarbonate solution, dried, and finally evaporated under reduced pressure to give methyl 3-(3-hydroxybenzoyl)propionate (41g, 96m.p. 101.5°–103° C). On recrystallisation from toluene, the pure ester had m.p. 102°–103.5° C.

(Found: C, 63.57: H, 5.85; M⁺, 208. $C_{11}H_{12}O_4$ requires: C, 63.45: H, 5.81%, M, 208).

ii. A well stirred mixture of methyl 3-(3-hydroxybenzoyl)propionate (32g, 0.15 mole), allyl bromide (26 ml, 0.31 mole), potassium carbonate (21.2g, 0.15 mole), and dry acetone (500 ml) was heated under reflux for 8 hours. The mixture was filtered and the filtrate evaporated under reduced pressure leaving an oil (38.3g) which was dissolved in ether and washed with dilute sodium hydroxide solution and with water. Evaporation of the dried solution gave an oil (37.7g) which crystallised in the cold. The solid was triturated with petroleum ether (B.p. 60°–80° C) then collected to give methyl 3-(3-allyloxybenzoyl)Propionate (34.2g, 93% m.p. 30°–32.5° C).

iii. Methyl 3-(3-allyloxybenzoyl)propionate (5g) was heated under an atmosphere of nitrogen in an oil bath (temperature 220° C) for 4 hours, to give an oil which was purified on a silica column by elution with chloroform. Methyl 3-(2-allyl-3-hydroxybenzoyl)propionate was obtained as an oil (2.25g, 45%), and methyl 3-(4-allyl-3-hydroxybenzoyl)propionate as a solid m.p. 90°–92.5° C. (1.3g, 26%).

iv. Hydrazine hydrate (4.5 ml, 0.09 mole) was added to a stirred solution of methyl 3-(4-allyl-3-hydroxybenzoyl)propionate (5.6g, 0.023 mole) in glacial acetic acid (60 ml) and the mixture heated under reflux for one hour. Evaporation under reduced pressure gave a residue which was triturated with water to give 6-(4-allyl-3-hydroxyphenyl)-4,5-dihydro-3(2H)-pyridazinone (5g, m.p. 175°–178° C, 96%). The pure pyridazinone, recrystallised from ethanol had m.p. 178°–180° C.

Found: C, 68.09: H, 6.17; N, 12.34; M⁺, 230. $C_{13}H_{14}N_2O_2$ requires: C, 67.13; H, 6.13; N, 12.17%, M, 230).

v. By subjecting 6-(4-allyl-3-hydroxyphenyl)-4,5-dihydro-3(2H)-pyridazinone to a series of reactions similar to those described in Example 1(b), the title compound may be produced.

b. i. A stirred mixture of finely powdered 6-(3-hydroxyphenyl)-4,5-dihydro-3(2H)-pyridazinone (13.1g, 0.07 mole), potassium carbonate (9.5g, 0.07 mole), allyl bromide (11.75 ml, 0.14 mole), and dry acetone (250 ml) was heated under reflux for 18 hours. Evaporation of the filtered solution under reduced pressure gave 6-(3-allyloxyphenyl)-4,5-dihydro-3(2H)-pyridazinone which was washed with ether (13.66g, 86%, m.p. 111°–113° C). Crystallisation from a small volume of ethanol gave the pure pyridazinone m.p. 112°–114° C.

(Found: C, 67.51; H, 6.12; N, 12.19; m⁺, 230. $C_{12}H_{14}N_2O_2$ requires: C, 67.81; H, 6.13; N, 12.17%. M, 230).

ii. A mixture of 6-(3-allyloxyphenyl)-4,5-dihydro-3(2H)-pyridazinone (10g) and redistilled N,N-dimethylaniline (25 ml) was heated under reflux in an atmosphere of nitrogen for 6 hours. The dark solution was evaporated under reduced pressure to a semi-solid, which was diluted with ether and collected (9.5g). The phenolic components were purified by column chromatography to give 6(4-allyl-3-hydroxyphenyl)-4,5-dihydro-3(2H)-pyridazinone (m.p. 178°–180° C) and 6-(2-allyl-3-hydroxyphenyl)-4,5-dihydro-3(2H)-pyridazinone (m.p. 197°–200° C)

iii. By subjecting 6-(4-allyl-3-hydroxyphenyl)-4,5-dihydro-3(2H)-pyridazinone to a series of reactions similar to those described in Example 1 (b), the title compound may be produced.

EXAMPLE 7

Preparation of 6-[3-Allyl-4-(2-hydroxy-3-isopropylaminopropoxy)-phenyl]-4,5-dihydro-3(2H)-pyridazinone a. i. A stirred mixture of 2-allyl-4-bromophenol (15g, 0.07 mole), potassium carbonate (9.75g, 0.07 mole), benzyl chloride (8.9g, 0.07 mole), and acetone (20 ml) was heated under reflux for seven hours. The reaction mixture was then diluted with water and extracted with ether. The extract was washed with dilute sodium hydroxide (2 × 10 ml) and with water. Evaporation of the dried solution gave an oil (19.3g) which was distilled to give 3-allyl-4-benzyloxybromobenzene (13.97g, 65%), b.p. 166°–168° C/1.5 mm.

(Found: C, 63.66; H, 4.86 $C_{16}H_{15}BrO$ requires: C, 63.39; H, 4.99%).

ii. By subjecting 3-allyl-4-benzyloxybromobenzene to a series of reactions similar to those described in Example 1(a), the title compound may be produced.

b. i. A stirred mixture in dry acetone (50 ml), 6-(4-hydroxyphenyl)-4,5-dihydro-3(2H)-pyridazinone (7g, 0.037 mole), allyl bromide (3.2ml, 0.037 mole) and potassium carbonate (5.1g, 0.037 mole) was heated under reflux for 14 hours. The mixture was diluted with acetone and filtered hot. The inorganic residue was washed with warm acetone and the combined washings and filtrate were evaporated under reduced pressure. The residue was broken up with ether, collected and washed with ether to give 6-(4-allyl-oxyphenyl)-4,5-dihydro-3(2H)-pyridazinone (6.88 g, 81%, m.p. 130.5°–132° C). Recrystallisation from methanol gave fine white needles of m.p. 134°–135° C.

Found: C, 67.85; H, -6.02; N, 12.03; M⁺, 230. $C_{13}H_{14}N_2O_2$ requires: C, 67.81; H, 6.13; N, 12.17%; M, 230).

ii. A mixture of 6(4-allyloxyphenyl)-4,5-dihydro-3(2H)-pyridazinone (81.8g, 0.36mole; and N,N-dimethylaniline (200 ml) was heated under reflux in an atmosphere of nitrogen for 6 hours, then allowed to cool overnight. The collected product was well washed with ether to give 6-(3-allyl-4-hydroxyphenyl)-4,5-dihydro-3(2H)-pyridazinone (71.5g, 87%, m.p. 240°–244° C). Recrystallisation from 2-methoxyethanol gave the pure material of m.p. 242°–244° C. (Found: C, 67.54; H, 6.20; N, 12.04; M⁺, 230. $C_{13}H_{14}N_2O_2$ requires: C, 67.81; H, 6.13; N, 12.17%, M, 230).

iii. A mixture of finely ground 6-(3-allyl-4-hydroxyphenyl)-4,5-dihydro-3(2H)-pyridazinone (50g, 0.22 mole), epichlorohydrin (200 g, 2.2 mole) and piperidine (2g) was heated on a steam bath for 90 minutes. Evaporation under reduced pressure gave a viscous oil which was dissolved in dichloromethane and stirred for 10 minutes with dilute sodium hydroxide (500 ml). The organic phase was washed with water, dried and evaporated to an oil which slowly solidified. Addition of ethanol-ether gave 6[3-allyl-4-(2,3-epoxypropoxy)-phenyl]-4,5-dihydro-3(2H)-pyridazinone (30g, 47%, m.p. 92.5°–95° C) which was recrystallised from aqueous ethanol to give the pure pyridazinone (m.p. 93.5°–95° C).

Found: C, 67.41; H, 6.47; N, 9.80; M$^+$, 286. $C_{16}H_{18}N_2O_3$ requires: C, 67.11; H, 6.33; N, 9.79%. M, 286).

iv. A stirred mixture of 6-[3-allyl-4-(2,3-epoxypropoxy)-phenyl]-4,5-dihydro-3(2H)-pyridazinone (46g, 0.16 mole), methanol (500 ml) and isopropylamine (85 ml, 1 mole) was heated under reflux for 60 minutes. Evaporation of the solution under reduced pressure gave an oil (66 g) which was purified on a silica column by elution with mixtures of chloroform and methanol to give 6-[3-allyl-4-(2-hydroxy-3-isopropylaminopropoxy)phenyl]-4,5-dihydro-3(2H)-pyridazinone (45g, 85%, m.p. 94°–96.5° C). The hemisulphate hemihydrate, crystallised from aqueous ethanol, had m.p. 238°–242° C.

(Found: C, 56.81; H, 7.02; N, 10.04; $SO_4$, 11.63; M$^+$, 345. $C_{19}H_{27}N_3O_3 \cdot \frac{1}{2}H_2SO_4 \cdot \frac{1}{2}H_2O$ requires: C, 56.56; H, 7.24; N, 10.41; $SO_4\frac{1}{2}$, 11.90%. M(base), 345).

Example 8

Preparation of
6-[4-(3-t-Butylamino-2-hydroxypropoxy)-3-chlorophenyl]-4,5-dihydro-3(2H)-pyridazinone i. Aluminium chloride powder (66.75g, 0.5 mole) was added during one hour to a stirred mixture of dry 2-chlorophenol (27.3g, 0.22 mole), powdered succinic anhydride (20g, 0.2 mole) and dry sym-tetrachlorethane (150 ml) while the temperature was allowed to rise from 20° C to 40° C. The resultant mixture was heated in an oil bath at 135° C for 2 hours, then cooled in ice and hydrolysed with cold 10% hydrochloric acid solution (100 ml). Tetrachloroethane was removed by steam distillation and the aqueous residue precipitated a gum which was purified by standard procedures to give 31.97g, 70%, of a mixture of 3-(3-chloro-2-hydroxybenzoyl) propionic acid and 3-(3-chloro-4-hydroxybenzoyl)propionic acids. Esterification of the mixed acids with methanol - hydrogen chloride and separation of the products by column chromatography (silica, 5/1 chloroform/petroleum ether B.p. 60°–80° C) gave methyl 3-(3-chloro-2-hydroxybenzoyl)propionate (m.p. 60°–62° C) and methyl 3-(3-chloro-4-hydroxybenzoyl)propionate (m.p. 85°–89° C). Hydrolysis of the latter ester with dilute sodium hydroxide solution gave 3-(3-chloro-4-hydroxybenzoyl)propionic acid (m.p. 155°–160° C). The pure acid, on recrystallisation from water, had m.p. 160°–162° C.

(Found- C, 52.69; H, 3.94; Cl, 15.73; M$^+$, 228/230. $C_{10}H_9ClO_4$ requires: C, 52.52; H, 3.97; Cl, 15.51%, M, 228/230).

ii. Hydrazine hydrate (1.5 ml, 0.03 mole) was added to a stirred suspension of 3-(3-chloro-4-hydroxybenzoyl)propionic acid (4.4g, 0.02 mole) in water (25 ml) and the mixture heated under reflux for 1 hour. The resultant mixture was diluted with water (25 ml) and allowed to cool. 6-(3-chloro-4-hydroxyphenyl)-4,5-dihydro-3(2H)-pyridazinone (4.09g, 95%, m.p. 272°–278° C) was collected and well washed with water. Recrystallisation from 2-methoxyethanol gave the pure pyridazinone m.p. 277°–281° C.

(Found: C, 53.34; H, 4.02; N, 12.37; $C_{10}H_9ClN_2O_2$ requires: C, 53.46; H, 4.04; N, 12.47%).

iii. A mixture of powdered 6-(3-chloro-4-hydroxyphenyl)-4,5-dihydro-3(2H)-pyridazinone (3g, 0.013 mole), epichlorohydrin (24g, 0.24 mole), and piperidine (6 drops) was heated on a steam bath for 4.5 hours. Evaporation of the solution gave an oil (5.84g) which was dissolved in dichloromethane and stirred with dilute sodium hydroxide solution (30 ml). The organic solution was washed with water, dried, and evaporated to give the crude epoxide (3.5g, 95%). Column chromatography (silica, chloroform-methanol mixtures) gave pure 6-[3-chloro-4-(2,3-epoxypropoxy)phenyl]-4,5-dihydro-3(2H)-pyridazinone (2.9g, 78%, m.p. 147.5°–149° C). The melting point was (2.9g, 78%, m.p. 147.5°–149° C). The melting point was unchanged after recrystallisation from ethanol.

(Found: C, 55.55; H, 4.63; Cl, 12.65; N, 9.97; M$^+$, 280/282. $C_{13}H_{13}ClN_2O_3$ requires: C, 55.62; H, 4.67; Cl, 12.63; N, 9.98%, M, 280/282).

iv. A stirred mixture of 6-[3-chloro-4-(2,3-epoxypropoxy)-phenyl]-4,5-dihydro-3(2H)-pyridazinone (2.91g, 0.01 mole) methanol (58 ml), and t-butylamine (6.6ml, 0.06 mole) was heated under reflux for 90 minutes. Evaporation of the solution under reduced pressure gave a glassy solid, 3.79g. The hydrochloride (m.p. 229°–238° C decomposition) was recrystallised from ethanol-ether to give pure 6-[4-(3-t-butylamino-2-hydroxypropoxy)-3-chlorophenyl]-4,5-dihydro-3(2H)-pyridazinone hydrochloride m.p. 234°–238° C (decomposition).

(Found: C, 52.13; H, 6.49; N, 10.36 $C_{17}H_{24}ClN_3O_3 \cdot HCl$ requires: C, 52.31; H, 6.46; N, 10.77%).

EXAMPLE 9

Preparation of
6-[3-Chloro-4-(2-hydroxy-3-isopropylaminopropoxy)-phenyl]-4,5-dihydro-3(2H)-pyridazinome i. In a similar reaction to that described in Example 7 a(i) 4-bromo-2-chlorophenol gave 4-benzyloxy-3-chlorobromobenzene (15.3g, 71%) which after crystallisation from petroleum ether (b.p. 40°–60° C) had m.p. 59.5°–60° C.

(Found: C, 52.34; H, 3.31. $C_{13}H_{10}BrClO$ requires: c, 52.45; H, 3.39%).

ii. By subjecting 4-benzyloxy-3-chlorobromobenzene to a series of reaction similar to those described in Example 1(a), the title compound may be produced.

EXAMPLE 10

Preparation of 6-[3-(2-Hydroxy-3-isopropylaminopropoxy)phenyl]-4,5-dihydro-3(2H)-pyridazinone i. A mixture of finely powdered 6-(3-hydroxyphenyl)-4,5-dihydro-3(2H)-pyridazinone (21.6g, 0.11mole), epichlorohydrin (90ml, 1.1 mole), and piperidine (1 ml) was heated on a steam bath for 90 minutes. Evaporation of the solution under reduced pressure gave an oil which was dissolved in dichloromethane and stirred with dilute sodium hydroxide solution (60 ml). The organic phase was washed with water, dried, and evaporated under reduced pressure to a viscous oil (27g, 96%). Purification on a silica column by elution with chloroform gave 6-[3-(2,3-epoxypropoxy)phenyl]-4,5-dihydro-3(2H)-pyridazinone (16.5g, 59%) as an oil which when treated with ether gave a white solid (13.7g, 49%, m.p. 108°–112° C). The pure epoxide, recrystallised from methanol petroleum/ether (b.p. 60°–80° C), had m.p. 110°–112° C.
(Found: C, 63.96; H, 5.70; N, 11.43: M$^+$, 246. $C_{13}H_{14}N_2O_3$ requires: C, 63.39; H, 5.73; N, 11.38%. M, 246).

ii. A stirred mixture of 6-[3-(2,3-epoxypropoxy)-phenyl]-4,5-dihydro-3(2H)pyridazinone (10g, 0.04 mole), methanol (100 ml), and isopropylamine (20.8 ml, 0.24 mole) was heated under reflux for 90 minutes. Evaporation of the solution under reduced pressure gave a white solid (12.5 g, 100%) which when treated with ether, gave crude 6-[3-(2-hydroxy-3-isopropylaminopropoxy)phenyl]-4,5-dihydro-3(2H)-pyridazinone (11.7g, 94%, m.p. 137°–141° C). The hemisulphate, on recrystallisation from aqueous methanol/ether, had m.p. 256°–258° C.

(Found: C, 53.88; H, 6.67; N, 11.63; SO$_4$, 13.49; M$^+$, 305. C$_{16}$H$_{23}$N$_3$O$_3$.½H$_2$SO$_4$ requires: C, 54.22; H, 6.83; N, 11.86; SO$_4$ 13.55%. M(base) 305).

EXAMPLE 11

Preparation of 6-[4-(3-t-Butylamino-2-hydroxypropoxy)-3-methoxyphenyl]-4,5-dihydro-3(2H)-pyridazinone i. A mixture of powdered 6-(4-hydroxy-3-methoxyphenyl)-4,5-dihydro-3(2H)-pyridazinone (1.83g, 0.008 mole), epichlorohydrin (15g, 0.16 mole), and piperidine (3 drops) was heated on a steam bath for 90 minutes. Evaporation under reduced pressure gave an oil (3.54g) which was dissolved in dichloromethane and stirred with dilute sodium hydroxide solution (4.5 ml). The organic solution was washed with water, dried, and evaporated under reduced pressure to an oil (2.7g). Purification by column chromatography (silica, chloroform) gave 6-[4-(2,3-epoxypropoxy)-3-methoxyphenyl]-4,5-dihydro-3(2H)-pyridazinone (2.13g, 93%, m.p. 134°–136.5° C) which when recrystallised from ethanol and well dried, had m.p. 133°–137° C.

(Found: C, 60.64; H, 5.80; N, 9.95; M$^+$, 276. C$_{14}$H$_{16}$N$_2$O$_4$ requires: C, 60.86; H, 5.84; N, 10.14%, M, 276).

ii. A stirred mixture of 6-[4-(2,3-epoxypropoxy)-3-methoxyphenyl]-4,5-dihydro-3(2H)-pyridazinone (1.2g, 0.0043 mole), methanol (24 ml), and t-butylamine (2.76 ml, 0.026 mole) was heated under reflux for 90 minutes. Evaporation of the solution under reduced pressure gave a glassy residue (1.44g, 95%). The crude hemisulphate of 6-[4-(3-t-butylamino-2-hydroxypropoxy)-3-methoxyphenyl]-4,5-dihydro-3(2H)-pyridazinone (m.p. 266°–268.5° C) was recrystallised from methanol-ether to give the pure hemisulphate m.p. 270°–272° C decomposition.

(Found: C, 52.88; H, 6.91; N, 10.14; S, 3.90. C$_{18}$H$_{27}$N$_3$O$_4$.½H$_2$SO$_4$ 2/3H$_2$O: requires: C, 52.67; H, 7.20; N, 10.24; S, 3.91%).

EXAMPLE 12

Preparation of 6-[3-3-t-Butylamino-2-hydroxypropoxy)-4-methylphenyl]-4,5-dihydro-3(2H)-pyridazinone i. A stirred suspension of 3-(3-hydroxy-4-methylbenzoyl) propionic acid (6.75g, 0.032 mole) in water (40ml) was treated with hydrazine hydrate (2.4 ml, 0.048 mole) and heated under reflux for one hour. The mixture was diluted with water (50 ml), cooled, and the product collected then washed with water. (6.36g, 96%, m.p. 215°–218° C). Crystallisation from ethanol gave pure 6-(3-hydroxy-4-methylphenyl)-4,5-dihydro-3(2H)-pyridazinone, m.p. 216°–218° C.

(Found: C, 64.80; H, 5.94; n, 13.52; M$^+$, 204. C$_{11}$H$_{12}$N$_2$O$_2$ requires: c, 64.69; H, 5.92; N, 13.72%, M, 204).

ii. A mixture of powdered 6-(3-hydroxy-4-methylphenyl)-4,5-dihydro-3(2H)-pyridazinone (5.0g, 0.024 mole), epichlorohydrin (19.3 ml, 0.24 mole), and piperidine (0.2 ml) was heated on a steam bath for one hour. Evaporation of the solution under reduced pressure gave an oil which was dissolved in a small volume of dichloromethane and stirred with dilute sodium hydroxide solution (15 ml). The organic phase was washed with water, dried, and evaporated to an oil which under reduced pressure gave a solid, 6.2g, 98%. Trituration with ethanol-ether gave crude 6-[3-(2,3-epoxypropoxy)-4-methylphenyl]-4,5-dihydro-3(2H)-pyridazinone 4.81g, 76%, m.p. 128°–132° C. Purification, by recrystallisation from ethanol, or by column chromatography (silica, chloroform) gave the pure epoxide, m.p. 140°–142.5° C.

(Found: C, 64.69; H, 6.26; N, 10.70; M$^+$, 260. C$_{14}$H$_{16}$N$_2$O$_3$ requires: C, 64.60; H, 6.20; N, 10.76%, M, 260).

iii. A stirred mixture of 6-[3-(2,3-epoxypropoxy)-4-methylphenyl]-4,5-dihydro-3(2H)-pyridazinone (3.3g, 0.013 mole) methanol (33 ml) and t-butylamine (8 ml, 0.076 mole) was heated under reflux for 75 minutes. Evaporation of the solution under reduced pressure gave a gum which when treated with ether, solidified 4.27g, 100%, m.p. 153°–158° C. 6-[3-(3-t-Butylamino-2-hydroxypropoxy)-4-methylphenyl]-4,5-dihydro-3(2H)-pyridazinone was purified as its hemisulphate m.p. 274°–276° C (decomposition), which recrystallised from aqueous ethanol had m.p. 275°–277° C (decomposition).

Found: C, 56.51; H, 7.35; N, 10.83; SO$_4$, 12.84; M$^+$, 333. C$_{18}$H$_{27}$N$_3$O$_3$.½H$_2$SO$_4$. requires: C, 56.53; H, 7.38; N, 10.98; SO$_4$, 12.55% M(base), 333).

EXAMPLE 13

Preparation of 6-[4-(2-Hydroxy-3-isopropylaminopropoxy)-3-nitrophenyl]-4,5-dihydro-3(2H)-pyridazinone i. Powdered 3-(4-hydroxybenzoyl)propionic acid (7.47g, 0.038 mole was added during 35 minutes to well stirred fuming nitric acid (15 ml) cooled to between −10° to −5° C. The solution was stirred for an additional 10 minutes at −5° C, poured into ice-water (400 ml) and the crude product collected and washed with water (8.22g. 89%, m.p. 150°–165° C). 6-(3,5-Dinitro-4-hydroxybenzoyl)propionic acid (m.p. 184°–188° C) was removed by passage through a short silica column, to give 6-(4-hydroxy-3-nitrobenzoyl)propionic acid, which on recrystallation from water had m.p. 172°–174° C. (Found: C, 50.12; H, 3.85; N, 5.60M$^+$, 239. C$_{10}$H$_9$NO$_6$ requires: C, 50.21; H, 3.79; N, 5.86%, M, 239).

ii. Hydrazine hydrate (0.775 ml, 0.015 mole) was added to a stirred suspension of 3-(4-hydroxy-3-nitrobenzoyl) propionic acid (3.7g, 0.015 mole) in water (37 ml) and the mixture heated under reflux for one hour. The resultant mixture was diluted with water, cooled, and the product collected and washed with water (3.31g, 91%, m.p. 253°–257° C decomposition). 6-(4-Hydroxy-3-nitrophenyl)-4,5-dihydro-3(2H)-pyridazinone recrystallized from 2-methoxyethanol had m.p. 251°–257° C (decomposition).

Found: C, 50.78; H, 3.92; N, 18.05; M$^+$, 235. C$_{10}$H$_9$N$_3$O$_4$ requires: C, 51.06; H, 3.86; N, 17.87%; M, 235).

iii. A mixture of powdered 6-(4-hydroxy-3-nitrophenyl-4,5-dihydro-3(2H)-pyridazinone (3.09g, 0.013 mole), epichlorohydrin (18g, 0.195 mole), and piperdine (4 drops), was heated on a steam bath for 5 hours.

The cold mixture was diluted with ether and a mixture of 6-[4-(2,3-epoxypropoxy)-3-nitrophenyl]-4,5-dihydro-3(2H)-pyridazinone and 6-[4-(3-chloro-2-hydroxypropoxy)-3-nitrophenyl]-4,5-dihydro-3(2H)-pyridazinone collected (3.41g, m.p. 145°–158°C). Evaporation of the filtrate under reduced pressure gave an additional 0.54g, m.p. 150°–158°C. Treatment of the mixed product with potassium carbonate in dimethylformamide gave the crude epoxide m.p. 140°–145°C.

iv. A mixture of 6-[4-(2,3-epoxypropoxy)-3-nitrophenyl]-4,5-dihydro-3(2H)-pyridazinone and 6-[4-(3-chloro-2-hydroxypropoxy)-3-nitrophenyl]-4,5-dihydro-3(2H)-pyridazinone (0.9g) was stirred with methanol (9 ml) and isopropylamine (1.6 ml) and heated under reflux for 60 minutes. Evaporation under reduced pressure gave a glassy solid, 0.96g, from which 6-[4-(2-hydroxy-3-isopropylaminopropoxy)-3-nitrophenyl]-4,5-dihydro-3(2H)-pyridazinone was isolated as its hydrochloride (m.p. 210°–215° C) by column chromatography (silica, chloroform-methanol mixtures).

(Found: M+, 350. $C_{16}H_{22}N_4O_5.HCl$ requires: M(base),350).

EXAMPLE 14

Preparation of
6-[4-(3-t-Butylamino-2-hydroxypropoxy)-3-nitrophenyl]-4,5-dihydro-3(2H)-pyridazinone i. A stirred mixture of crude 6-[4-(2,3-epoxypropoxy)-3-nitrophenyl]-4,5-dihydro-3(2H)-pyridazinone (3.3g, 0.011 mole), methanol (70 ml), and t-butylamine (7.2 ml, 0.068 mole), was gently heated under reflux for 105 minutes. The filtered solution was evaporated under reduced pressure to an orange coloured foam (4g, 97%). The crude base (3.77g) was digested with water (200 ml) and glacial acetic acid added to pH 4, then the solution filtered and washed with dichloromethane (3 × 100 ml). The aqueous phase was treated with potassium carbonate solution to pH 9, then extracted with dichloromethane and the combined organic extracts washed with a little water. Evaporation of the dried solution gave crude 6-[4-(3-t-butylamino-2-hydroxypropoxy)-3-nitrophenyl]-4,5-dihydro-3(2)-pyridazinone (2,82g, m.p. about 92°–105° C). After two recrystallisations from ethyl acetate the free base (m.p. about 124° C) was converted into its hydrochloride m.p. 260°–262° C. The pure hydrochloride recrystallised from methanol-ether, had m.p. 263°–265° C (decomposition).

(Found: C, 50.66; H, 6.36; N, 13.71. $C_{17}H_{24}N_4O_5.HCl$ requires: C, 50.94; H, 6.29; N, 13.98%).

EXAMPLE 15

Preparation of
6-[4-(3-t-Butylamino-2-hydroxypropoxy)-3-morpholinophenyl]-4,5-dihydro-3(2H)-pyridazinone i. Ethylene oxide (7g, 0.16 mole) was added to a suspension of 2-amino-4-bromophenol (3.76g, 0.02 mole) in a mixture of acetic acid (1 ml), water (2 ml), and ethanol (10 ml) and the mixture was stirred overnight. Additional ethylene oxide (7g, 0.16 mole) was added and the mixture was stirred for 24 hours. The residue after evaporation under reduced pressure was dissolved in chloroform and washed with 10% ammonium hydroxide solution (2 × 10 ml). The combined aqueous phases were extracted with chloroform (2 × 10 ml) which was in turn washed with water (10 ml).

The combined chloroform solutions were dried and evaporated to give 4-bromo-2-N-bis(2-hydroxyethyl)aminophenol as a brown viscous oil (5g; 90%).

ii. 4-Bromo-2-bis(2-hydroxyethyl)aminophenol (2.5g) was dissolved in 70% sulphuric acid (25 ml) and the solution heated to 160° C for three hours, allowed to cool, then neutralised with saturated sodium carbonate solution. Extraction with ether and evaporation of the extracts gave crude 4-bromo-2-morpholinophenol which was crystallised from ether gave the pure phenol (1.4g, 60%, m.p. 128° C).

iii. A well stirred mixture of 4-bromo-2-morpholino phenol (4.44g, 0.017 mole), benzyl chloride (2.3 ml, 0.02 mole), potassium carbonate (4.75g, 0.034 mole), and dry acetone (60 ml) was heated under reflux for 7 hours. The mixture was diluted with water, extracted with ether and the combined extracts washed with dilute sodium hydroxide solution and with water. Extraction of the ethereal solution with concentrated hydrochloric acid and evaporation of these extracts under reduced pressure gave 4-benzyloxy-3-morpholinobromobenzene hydrochloride, which was collected and washed with ether (5.29g, 80%, m.p. 164°–174° C). The hydrochloride, recrystallised from ethanol, had m.p. 168°–177° C. A suspension of the hydrochloride in water was treated with excess potassium carbonate and 4-benzyloxy-3-morpholinobromobenzene extracted into ether. Evaporation of the ether extracts gave the free base, m.p. 84°–87° C.

iv. By subjecting 4-benzyloxy-3-morpholinobromobenzene to a series of reactions similar to those described in Example 1(a), the title compound may be produced.

EXAMPLE 16

Preparation of
6-[2-Allyl-3(2-hydroxy-3-isopropylaminopropoxy)-phenyl]-4,5-dihydro-3(2H)-pyridazinone i. Hydrazine hydrate (4.5 ml, 0.09 mole) was added to a stirred solution of methyl 3-(2-allyl-3-hydroxybenzoyl) propionate (1.9g, 0.0077 mole) in glacial acetic acid (20 ml) and the mixture heated under reflux for 8 hours. The solution was evaporated under reduced pressure leaving a viscous oil which was triturated with warm water to give crude 6-(2-allyl-3-hydroxyphenyl)-4,5-dihydro-3(2H)-pyridazinone (1.1g, 62%), identical with that obtained in Example 6(b) (ii).

ii. By subjecting 6-(2-allyl-3-hydroxyphenyl)-4,5-dihydro-3(2H)-pyridazinone to a series of reactions similar to those described in Example 7(b) (iii) (iv), the title compound may be produced.

EXAMPLE 17

Preparation of
6-[3-(2-Hydroxy-3-isopropylaminopropoxy)-4,5-dimethylphenyl]-4,5-dihydro-3(2H)-pyridazinone By subjecting 3-(3,4-dimethylbenzoyl)propionic acid to a series of reactions similar to those described in Example 25(i) 21(i)-(iii) the title compound may be produced.

EXAMPLE 18

Preparation of
6-[4-(3-t-Butylamino-2-hydroxypropoxy)-3-cyanophenyl]-4,5-dihydro-3(2H)-pyridazinone By subjecting 2-cyanophenol to a series of reactions similar to those described in Example 8, the title compound may be produced.

EXAMPLE 19

Preparation of
6-[5-Acetamido-2-(3-t-butylamino-2-hydroxypropoxy)phenyl]-4,5-dihydro-3(2H)-pyridazinone i. Nitric acid (d. 1.52; 50 ml) was added dropwise to a stirred suspension of 3-(2-hydroxybenzoyl)propionic acid (30g) in glacial acetic acid (250 ml) at 5°–10° C. The mixture was allowed to slowly warm up to 30°–35° C when heat was evolved and external cooling was necessary to keep the temperature of the reaction mixture below 45° C. When the exothermic phase of the reaction had subsided, the resulting solution was stirred for a further 60 minutes and then poured into ice-water (750 ml). The resulting yellow precipitate, a crude mixture of 3-(2-hydroxy-5-nitrobenzoyl)propionic acid and 3-(2-hydroxy-3-nitrobenzoyl)propionic acid, was washed with water, dried and used as such for the next reaction (36.0 g, m.p. 152–156; M+, 239, M,239).

ii. The above mixture of acids (60g) was dissolved in dry methanol (800 ml) and hydrogen chloride gas was passed through the gently boiling solution for 2 hours and the solent evaporated off under reduced pressure. Chloroform (200 ml) was added to the residue and the resulting solution was washed in turn with aqueous sodium bicarbonate (200 ml) and with water. The solution was then dried and evaporated under reduced pressure to give a solid residue (55g). Separation of the isometric esters was achieved by elution with chloroform and with chloroform/methanol mixtures from a silica column. Methyl 3-(2-hydroxy-5-nitrobenzoyl)propionate was thus obtained as a solid (25.3g, 40%). Crystallisation from carbon tetrachloride gave the product as needles m.p. 90°–93° C.

(Found: C, 52.16; H, 4.36; N, 5.38; M+, 253. $C_{11}H_{11}NO_6$ requires: C, 52.17; H, 4.38; N, 5.53%; M, 253).

iii. Methyl 3-(2-hydroxy-5-nitrobenzoyl)propionate (19.0 g) was dissolved in sodium hydroxide solution (2N; 600 ml) and the resulting solution was heated on a steam bath for 60 minutes. Acidification of the cooled solution by dilute hydrochloric acid gave 3-(2-hydroxy-5-nitrobenzoyl)propionic acid as a white solid which was washed with water and dried for use in the next reaction. (17.4g; m.p. 175°–178° C).

iv. A solution of 3-(2-hydroxy-5-nitrobenzyol)propionic acid (5.5g) in ammonium hydroxide solution (5N; 100 ml) was added to a stirred, boiling solution of ferrous sulphate heptahydrate (45g) in water (200 ml). Stirring under reflux was continued for a further 60 minutes, ammonium hydroxide solution was added until the mixture had pH 9, the reaction mixture filtered through Kieselguhr and the filtrate evaporated to dryness. The solid residue was crystallised from ethanol to give pale yellow needles of 3-(5-amino-2-hydroxybenzoyl)propionic acid (2.2g, 46%, m.p. 158°–160° C; M+,209, M, 209).

v. Sodium hydroxide solution (0.2 N) was added to 3-(5-amino-2-hydroxybenzoyl)propionic acid (2.4g) until all the solid had dissolved. Acetic anhydride (3.0 ml) was quickly added to the solution (pH 10) with vigorous stirring at 10°–15° C, after which the pH reading was in the range 4–5, and stirring was continued for a further 60 minutes. The precipitated solid was collected and washed with water and a second crop was obtained by evaporation of the filtrate and addition of water to the residue. The combined solids were recrystallised from ethanol to give 3-( 5-acetamido-2-hydroxybenzoyl)propionic acid (2.2g, 76%), m.p. 205°–206° C.

(Found: C, 57.13; H, 5.25; N, 5.57; M+, 251. $C_{12}H_{13}NO_5$ requires: C, 57.37; H, 5.22; N, 5.58%, M, 251).

vi. Hydrogen chloride gas was passed through a gently boiling solution of 3-(5-acetamido-2-hydroxybenzoyl) propionic acid (1.2g) in dry methanol (20 ml) until esterification was complete. The reaction mixture was then poured into ice-water and chloroform added. The chloroform extract was washed with sodium bicarbonate solution then water, and finally dried and evaporated to leave methyl 3-(5-acetamido-2-hydroxybenzoyl)propionate as a solid (0.75g, 59%; m.p. 145°–147° C; M+, 265, M 265).

vii. Methyl 3-(5-acetamido-2-hydroxybenzoyl)propionate (0.75g) anhydrous potassium carbonate (0.39g), epibromohydrin (0.78g) and dry methyl ethyl ketone (20 ml) were stirred and heated under reflux for 16 hours. The cooled reaction mixture was filtered, the filtrate evaporated under reduced pressure and the residual oil purified by elution from a silica column with chloroform/methanol. Methyl 3-[5-acetamido-2-(2,3-epoxypropoxy)benzoyl]propionate was obtained as an oil which solidified, (0.52g, 57%, m.p. 84°–87° C; M+, 321, M 321).

viii. A solution of methyl 3-[5-acetamido-2-(2,3-epoxypropoxy)benzoyl]propionate (0.52g), t-butylamine (20 ml) and methanol (10 ml) was heated under reflux for 16 hours. Evaporation of the reaction mixture left a residual oil which was dissolved in ethanol and ether was then added. Methyl 3-[5-acetamido-2-(3-t-butylamino-2-hydroxypropoxy) benzoyl]propionate was deposited as a crystalline solid. (0.21g, 33%; m.p. 127°–128° C; M+, 394, M 394).

ix. A solution of methyl 3-[5-acetamido-2-(3-t-butylamino-2-hydroxypropoxy)benzoyl]propionate (0.21g) and hydrazine hydrate (0.12 ml) in glacial acetic acid (5 ml) was heated under reflux of 16 hours. Evaporation of the reaction mixture under reduced pressure gave a glassy residue to which was added sodium hydroxide solution (2N, 10 ml). The resulting solution was extracted well with chloroform, the combined organic phases washed with water, dried and evaporated to give a white brittle residue which was recrystallised from isopropanol/ether to give 6-[5-acetamido-2-(3-t-butylamino-2-hydroxypropoxy)-phenyl]-4,5-dihydro-3(2H)-pyridazinone as a white solid (0.16g, 80% m.p. 102°–109° C; M+, 376, M 376).

EXAMPLE 20

6-[2-(3-t-Butylamino-2-hydroxypropoxy)-4-chlorophenyl]-4,5-dihydro-3(2H)-pyridazinone By subjecting 3-(4-chloro-2-hydroxybenzoyl)propionic acid to a series of reactions similar to those described in Example 2, the title compound may be produced.

EXAMPLE 21

Preparation of
6-[3-(3-t-Butylamino-2-hydroxypropoxy)-4-fluorophenyl]-4,5-dihydro-3(2H)-pyridazinone i. In a similar reaction to that described in Example 19 (iv), 3-(4-fluoro-3-nitrobenzoyl)propionic acid was reduced to 3-(3-amino-4-fluorobenzoyl)propionic acid.

ii. 3-(3-Amino-4-fluorobenzoyl)propionic acid was diazotised with sodium nitrite in sulphuric acid solution and the diazonium sulphate was decomposed in boiling sulphuric acid solution to give 3-(4-fluoro-3-hydroxybenzoyl)propionic acid.

iii. By subjecting 3-(4-fluoro-3-hydroxybenzoyl)propionic acid to a series of reactions similar to those desired in Example 8(ii–iv) the title compound may be produced.

EXAMPLE 22

Preparation of
6-[4-Allyloxy-3-(2-hydroxy-3-isopropylaminopropoxy)-phenyl]-4,5-dihydro-3(2H)-pyridazinone.

i. Ethyl 3-(3,4-dimethoxybenzoyl)propionate was demethylated with boron tribromide in dichloromethane at −80° C to give ethyl 3-(3,4-dihydroxybenzoyl)-pripionate, m.p. 116°–117° C.

ii. Ethyl 3-(3,4-dihydroxybenzoyl)propionate was selectively acylated with ethyl chloroformate in aqueous sodium hydroxide to give the 3-carbethoxyoxy derivative, which was refluxed in acetone with allyl bromide and potassium carbonate, and the product was hydrolysed to give 3-(4-alloyloxy-3-hydroxy-benzoyl)-propionic acid.

iii. 3-(4-Allyloxy-3-hydroxybenzoyl)propionic acid was subjected to a series of reactions similar to those in Example 2 to yield the title compound.

EXAMPLE 23

Preparation of
6-[2-(3-t-Butylamino-2-hydroxypropoxy)phenyl]-5-methyl-4,5-dihydro-3(2H)-pyridazinone i. A mixture of 2-hydroxypropiophenone (3.0g), dimethylamine hydrochloride (2.45g), paraformaldehyde (0.6g), concentrated hydrochloric acid (0.5 ml) and absolute ethanol (30 ml) was heated under reflux with stirring for 12 hours. The mixture was evaporated to dryness and the residue was treated with isopropanol. The resulting white solid was filtered off, washed with ether and dried to give 2-(3-dimethylamino-2-methylpropionyl)phenol hydrochloride (1.6g).

ii. A mixture of 2-(3-dimethylamino-2-methylpropionyl)phenol hydrochloride (2.70g), potassium cyanide (1.3g) and water (50 ml) was heated under reflux for 2 hours. The mixture was cooled, neutralised and extracted with chloroform. The extracts were dried (MgSO$_4$) and the solvent was evaporated and purified by chromatography on a silica column to give 2-(3-cyano-2-methylpropionyl)phenol as an orange oil (1.95g).

iii. 2-(3-Cyano-2-methylpropionyl)phenol was hydrolysed with aqueous alkali to give 3-(2-hydroxybenzoyl)butyric acid iv. By subjecting 3-(2-hydroxybenzoyl)-3-methylpropionic acid to a series of reactions similar to those in Example 2 the title compound may be prepared.

EXAMPLE 24

Preparation of
6-[-2-(3-t-Butylamino-2-hydroxypropoxy)-6-methoxyphenyl]-4,5-dihydro-3(2H)-pyridazinone i. 2,6-Dimethoxylithiobenzene was reacted with N-methylsuccinimide and the product was hydrolysed to give 3-(2,6-dimethoxybenzoyl)propionic acid.

ii. 2,6-Dimethoxyacetophenone was subjected to a series of reactions as described in Example 23 (i)-(iii) to give 3-(2,6-dimethoxybenzoyl)-propionic acid.

iii. 3-(2,6-Dimethoxybenzoyl)propionic acid was demethylated with boron tribromide according to the general procedure of Example 22(i) to give 3-(2,6-dihydroxybenzoyl)propionic acid.

iv. 3-(2,6-Dihydroxybenzoyl)propionic acid was esterified using methanol/hydrogen chloride and the ester was alkylated with methyl iodide to give methyl 3-(2-hydroxy-6-methoxy benzoylpropionate.

v. Methyl 3-(2-hydroxy-6-methoxy)benzoylpropionate was subjected to a series of reactions similar to those described in Example 2 to give the title compound.

EXAMPLE 25

Preparation of
6-[3-(2-Hydroxy-3-isopropylaminopropoxy)-4-morpholinophenyl]-4,5-dihydro-3(2H)-pyridazinone.

i. A suspension of 3-(4-fluorobenzoyl)propionic acid (50g) in nitric acid (d = 1.51, 500 ml) was stirred at −15° C for 30 minutes and poured into ice/water (2 l.). The precipitate was filtered off, washed with water and recrystallised from ethanol to give 3-(4-fluoro-3-nitrobenzoyl)-propionic acid (29.2g, 46%) as needles m.p. 136° C.

ii. A mixture of 3-(4-Fluoro-3-nitrobenzoyl)propionic acid (1.0g) morpholine (4.5 ml) and ethanol (12 ml) was heated under reflux overnight. The reaction mixture was evaporated under reduced pressure and the residue taken up into boiling ethanol. 3-(4-Morpholino-3-nitrobenzoyl)propionic acid crystallised on cooling as yellow rosettes (0.4g, 30%; m.p. 215° C).

iii. 3-(4-Morpholino-3-nitrobenzoyl)propionic acid was subjected to a series of reactions according to the general procedures of Examples 19(iv), 21(ii) and 8(ii–iv) to give the title compound.

EXAMPLE 26

Preparation of
6-[3-(3-t-Butylamino-2-hydroxypropoxy)-4-nitrophenyl]-5-methyl-4,5-dihydro-3(2H)-pyridazinone i. 3-Hydroxypropiophenone was added in portions to fuming nitric acid cooled in an ice-salt bath. The resultant mixture was stirred for an additional 30 minutes then poured into ice-water. 3-Hydroxy-4-nitropropiophenone was separated from the crude mixture of nitro-3-hydroxypropiophenones by column chromatography.

ii. 3-Hydroxy-4-nitropropiophenone was heated on a steam bath with acetic anhydride and a trace of pyridine until acetylation was complete. The residue, after evaporation of acetic anhydride under reduced pressure, was distributed between dichloromethane and water. Evaporation of the washed and dried dichloromethane solution gave 3-acetoxy-4-nitro-propiophenone.

iii. 3-Acetoxy-4-nitropropiophenone was added to a warm mixture of dimethylamine hydrochloride, aqueous formaldehyde, and acetic anhydride, and the mixture heated on a steam bath for 2 hours. Evaporation of the solution under reduced pressure gave a residue which was digested with hot acetone and the resultant mixture was evaporated under reduced pressure to a gum which was distributed between dichloromethane and water. The aqueous solution was separated and made alkaline with dilute sodium hydroxide solution and then extracted with dichloromethane. The combined organic extracts were washed with water, dried, and evaporated to give crude N,N-dimethyl 2-(3-acetoxy-4-nitrobenzoyl)propylamine. Quaternisation with iodomethane in acetone gave [2-(3-acetoxy-4-nitrobenzoyl)propyl]trimethylammonium iodide.

iv. A solution of [2-(3-acetoxy-4-nitrobenzoyl)propyl] trimethylammonium iodide in aqueous methanol was added to an aqueous solution of potassium cyanide, and the mixture was stirred for six hours. The solution was decanted from the crude product, 3-(3-acetoxy-4-nitrobenzoyl)butyronitrile, which was washed well with water and then hydrolysed with boiling 6N hydrochloric acid. Extraction of the acidic solution with dichloromethane and evaporation of the combined extracts gave 3-(3-acetoxy-4-nitrobenzoyl)butyric acid.

v. 3-(3-Acetoxy-4-nitrobenzoyl)butyric acid was dissolved in dilute sodium hydroxide solution, and the solution was warmed on a steam bath, cooled and acidified with hydrochloric acid to give 3-(3-hydroxy-4-nitrobenzoyl)butyric acid.

vi. By subjecting 3-(3-hydroxyl-4-nitrobenzoyl)butyric acid to a series of reactions similar to those described in Examples 13 (ii-iii) and 14, the title compound may be produced.

EXAMPLE 27

Preparation of 6-[3-(3-t-Butylamino-2-hydroxypropoxy)-4-cyanophenyl]-4,5-dihydro-3(2H)-pyridazinone a. i. 3-(4-Amino-3-nitrobenzoyl)propionic acid was diazotised in aqueous hydrochloric acid with sodium nitrite and the resultant solution treated with cuprous cyanide in potassium cyanide solution to give 3-(4-cyano-3-nitrobenzoyl)propionic acid, also available by a cyanide displacement reaction of 3-(4-fluoro-3-nitrobenzoyl)propionic acid.

ii. A solution of 3-(4-cyano-3-nitrobenzoyl)propionic acid in 5N ammonium hydroxide solution was added to a well stirred boiling aqueous solution of ferrous sulphate. The pH was adjusted to 9 with concentrated ammonium hydroxide solution and the mixture was refluxed for 15 minutes. The filtrate was concentrated and neutralised with glacial acetic acid to give 3-(3-amino-4-cyanobenzoyl)propionic acid.

iii. 3-(3-Amino-4-cyanobenzoyl)propionic acid was diazotised in aqueous sulphuric acid with sodium nitrite and the resultant solution was heated carefully until decomposition of the diazonium sulphate was complete. 3-(4-Cyano-3-hydroxybenzoyl)propionic acid was precipitated from the cooled solution.

iv. By subjecting 3-(4-cyano-3-hydroxybenzoyl)propionic acid to a series of reactions similar to those described in Example 8(ii-iv), the title compound may be produced.

b. i. 3-(3-Hydroxybenzoyl)propionic acid was nitrated by a method similar to that described in Example 13(i) to give a mixture of 3-(nitro-3-hydroxybenzoyl)propionic acids which were esterified with hydrogen chloride in methanol. Separation on a silica column by elution with chloroform-methanol mixtures gave methyl 3-(3-hydroxy-4-nitrobenzoyl)propionate.

ii. A mixture of methyl 3-(3-hydroxy-4-nitrobenzoyl)propionate, potassium carbonate, benzoyl chloride, and dimethylformamide was stirred overnight and the solvent removed by evaporation under reduced pressure. The residue was distributed between water and ether, and the aqueous phase was extracted with ether. The combined ethereal solution was washed in turn with dilute sodium hydroxide solution and water. Evaporation of the dried solution gave methyl 3-(3-benzyloxy-4-nitrobenzoyl)propionate.

iii. A stirred mixture of methyl 3-(3-benzyloxy-4-nitrobenzoyl)propionate and dilute sodium hydroxide solution was heated under reflux until all of the solid had dissolved. The cold solution was neutralised and 3-(3-benzyloxy-4-nitrobenzoyl)propionic acid was collected.

iv. A solution of 3-(3-benzyloxy-4-nitrobenzoyl)propionic acid in 5N ammonium hydroxide was added to a well stirred boiling aqueous solution of ferrous sulphate. The pH was adjusted to 9 with concentrated ammonium hydroxide and the mixture was refluxed for 15 minutes. The filtrate was concentrated under reduced pressure and then neutralised with glacial acetic acid to give 3-(4-amino-3-benzyloxybenzoyl)propionic acid.

v. 3-(4-Amino-3-benzyloxybenzoyl)propionic acid was diazotised in aqueous hydrochloric acid with sodium nitrite and the resultant solution was treated with cuprous cyanide in aqueous potassium cyanide solution to give 3-(3-benzyloxy-4-cyanobenzoyl)propionic acid.

vi. 3-(3-Benzyloxy-4-cyanobenzoyl)propionic acid was warmed with 33% hydrogen bromide in acetic acid and the solution was poured into ice-water to give 3-(4-cyano-3-hydroxybenzoyl)propionic acid.

vii. By subjecting 3-(4-cyano-3-hydroxybenzoyl)propionic acid to a series of reactions similar to those described in Example 8(ii-iv), the title compound may be produced.

EXAMPLE 28

Preparation of 6-[4-(3-t-Butylamino-2-hydroxypropoxy)-3-hydroxyphenyl]-4,5-dihydro-3-(2H)-pyridazinone Ethyl 3-(3,4-dihydroxybenzoyl)propionate was selectively acylated with ethyl chloroformate in the 3-position as in Example 22(ii), then converted as in Examples 2(ii) and 3(i), into ethyl 3-[4-(3-t-butylamino-2-hydroxypropoxy)-3-ethyloxycarbonyloxybenzoyl]propionate. Hydrolysis of the ester followed by cyclisation of the product with hydrazine hydrate as in Example 2(iv) gave the title compound.

EXAMPLE 29

Preparation of 6-[5-Amino-2-(3-t-butylamino-2-hydroxypropoxy)-phenyl]-4,5-dihydro-3(2H)-pyridazinone.

Methyl 3-[5-acetamido-2-(3-t-butylamino-2-hydroxypropoxy)benzoyl]propionate was hydrolysed by aqueous acid and the solution was neutralised and evaporated to dryness. 3-[5-Amino-2-(3-t-butylamino-2-hydroxypropoxy)benzoyl]propionic acid was extracted from the residue with hot ethanol and the combined extracts were evaporated to give the crude acid, which was cyclised by hydrazine hydrate as in Example 2(iv) to give 6-[5-amino-2-(3-t-butylamino-2-hydroxypropoxy)phenyl]-4,5-dihydro-3(2H)-pyridazinone.

EXAMPLE 30

Preparation of
6-[4-Dimethylamino-3-(2-hydroxy-3-isopropylaminopropoxy)phenyl]-4,5-dihydro-3(2H)-pyridazinone By subjecting 3-(4-fluoro-3-nitrobenzoyl)propionic acid to a series of reactions similar to those described in Example 25(ii-iii), but using dimethylamine in place of morpholine, the title compound may be produced.

EXAMPLE 31

Preparation of
6-[3-Amino-4-(3-t-butylamino-2-hydroxypropoxy)-phenyl]-4,5-dihydro-3(2H)-pyridazinone 6-[4-(3-t-Butylamino-2-hydroxypropoxy)-3-nitrophenyl]-4,5-dihydro-3(2H)-pyridazinone was reduced over 10% palladium on charcoal with excess hydrazine hydrate in ethanol to give the title compound.

EXAMPLE 32

Preparation of
6-[2-(3-t-Butylamino-2-hydroxypropoxy)-5-(methylamino)phenyl]-4,5-dihydro-3(2H)-pyridazinone i. 3-[5-Amino-2-(3-t-butylamino-2-hydroxypropoxy)benzoyl]propionic acid was esterified with hydrogen chloride in methanol. Evaporation of the solution under reduced pressure gave a residue which was dissolved in the minimum of water and the solution was neutralised with sodium carbonate and extracted with dichloromethane. The combined extracts were washed with saturated brine, dried, and evaporated to give methyl 3-[5-amino-2-(3-t-butylamino-2-hydroxypropoxy)benzoyl]propionate.

ii. A solution of methyl 3-[5-amino-2-(3-t-butylamino-2-hydroxypropoxy)benzoyl]propionate in dichloromethane was treated with excess of trifluoroacetic anhydride and potassium carbonate and the mixture was stirred until the reaction was complete. Water was added to the mixture and the separated aqueous phase was washed with dichloromethane. The combined organic extracts were washed with water, dried, and evaporated to give methyl 3[5-trifluoroacetylamino-2-(3-N-trifluoroacetyl-t-butylamino-2-trifluoroacetoxypropoxy)benzoyl]propionate.

iii. Methyl 3-[5-trifluoroacetylamino-2-(3-N-trifluoroacetyl-t-butylamino-2-trifluoroacetoxypropoxy)benzoyl]propionate was heated under reflux for 10 minutes with an excess of methyl iodide was powdered potassium hydroxide in dry acetone. Methyl iodide and the solvent were removed under reduced pressure and the residue was heated under reflux with water for 10 minutes. The solution was neutralised and evaporated under reduced pressure. The residue was extracted with hot ethanol, and the extracts were evaporated under reduced pressure to give 3-[2-(3-t-butylamino-2-hydroxypropoxy)-5-(methylamino)benzoyl]propionic acid.

iv. By subjecting 3-[2-(3-t-butylamino-2-hydroxypropoxy)-5-(methylamino)benzoyl]propionic acid to cyclisation with hydrazine hydrate by a method similar to that described in Example 19(ix), the title compound may be prepared.

EXAMPLE 33

Preparation of
6-[4-(3-t-butylamino-2-hydroxypropoxy)-3-trifluoromethylphenyl]-4,5-dihydro-3(2H)-pyridazinone By subjecting 2-trifluoromethylphenol to a series of reactions similar to those described in Example 8, the title compound may be produced.

EXAMPLE 34

| Ingredients | Amounts |
|---|---|
| 6-[5-Acetylamino-2-(3-t-butylamino-2-hydroxy propoxy)phenyl]4,5-dihydro-3-(2H)-pyridazinone | 150 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 35

| | |
|---|---|
| 6-[5-Acetylamino-2-(3-t-butylamino-2-hydroxy propoxy)phenyl]4,5-dihydro-3-(2H)-pyridazinone | 200 mg |
| Lactose | 100 mg |

The ingredients are screened, mixed and filled into a hard gelatin capsule.

What is claimed is:
1. A pharmaceutical composition having β-adrenergic blocking activity comprising in an effective amount to produce said activity a pyridazinone compound of the formula:

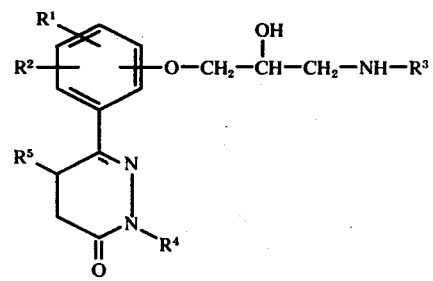

wherein
R¹ is hydrogen, lower alkyl, lower alkenyl, —CF₃, halogen, cyano, nitro, hydroxy, lower alkoxy, lower alkenyloxy, amino, lower alkanoylamino, lower alkylamino, di lower alkylamino or morpholino;
R² is hydrogen, methyl, or together with R¹ forms a benzene ring fused to the benzene ring shown to form a naphthyl group;
R³ is isopropyl or tertiary butyl; and
R⁴ and R⁵, which may be the same or different, are hydrogen or methyl;

or a pharmaceutically acceptable acid addition salt thereof in combination with a pharmaceutically acceptable diluent or carrier.

2. A method of inhibiting β-adrenergic receptors which comprises administering internally to an animal in need thereof in an amount sufficient to block said receptors a pyridazinone compound of the formula:

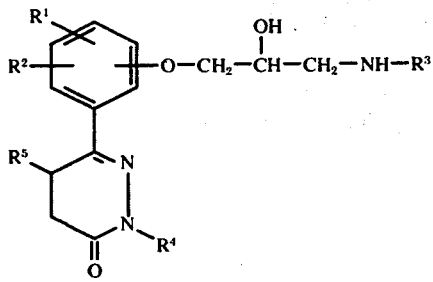

wherein
- $R^1$ is hydrogen, lower alkyl, lower alkenyl, —$CF_3$, halogen, cyano, nitro, hydroxy, lower alkoxy, lower alkenyloxy, amino, lower alkanoylamino, lower alkylamino, di lower alkylamino or morpholino;
- $R^2$ is hydrogen, methyl, or together with $R^1$ forms a benzene ring fused to the benzene ring shown to form a naphthyl group;
- $R^3$ is isopropyl or tertiary butyl; and
- $R^4$ and $R^5$, which may be the same or different, are hydrogen or methyl;

or a pharmaceutically acceptable acid addition salt thereof.

3. A method of concomitantly inhibiting β-adrenergic receptors and producing an acute antihypertensive effect which comprises administering internally to an animal in need thereof in an amount sufficient to block said receptors and produce said effect a pyridazinone compound of the formula:

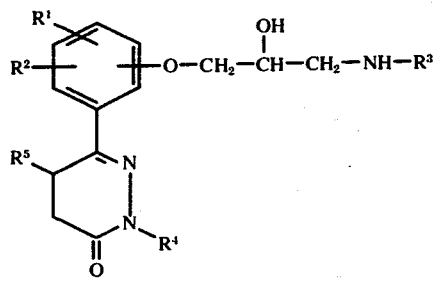

wherein
- $R^1$ is methyl, acetylamino, cyano or nitro;
- $R^2$ is hydrogen;
- $R^3$ is isopropyl or tertiary butyl; and
- $R^4$ and $R^5$, which may be the same or different, are hydrogen or methyl;

or a pharmaceutically acceptable acid addition salt thereof.

4. A method of treating angina pectoris which comprises administering internally to an animal in need thereof in an amount sufficient to alleviate the major symptoms of said condition a pyridazinone compound of the formula:

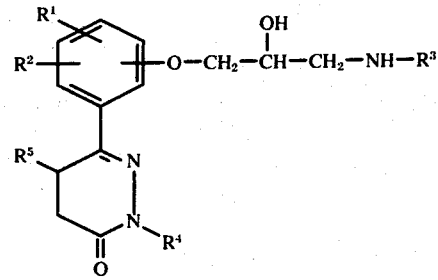

wherein
- $R^1$ is methyl, acetylamino, cyano or nitro;
- $R^2$ is hydrogen;
- $R^3$ is isopropyl or tertiary butyl; and
- $R^4$ and $R^5$, which may be the same or different, are hydrogen or methyl;

or a pharmaceutically acceptable acid addition salt thereof.

5. A method of treating cardiac arrhythmia which comprises administering internally to an animal in need thereof in an amount sufficient to alleviate the major symptoms of said condition a pyridazinone compound of the formula:

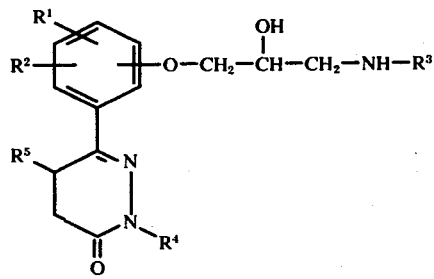

wherein
- $R^1$ is methyl, acetylamino, cyano or nitro;
- $R^2$ is hydrogen;
- $R^3$ is isopropyl or tertiary butyl; and
- $R^4$ and $R^5$, which may be the same or different, are hydrogen or methyl;

or a pharmaceutically acceptable acid addition salt thereof.

6. The pharmaceutical composition of claim 1 wherein the 3-alkylamino-2-hydroxy-1-propoxy side chain is ortho to the pyridazine ring and $R^1$ and $R^2$ are hydrogen.

7. The pharmaceutical composition of claim 1 wherein the 3-alkylamino-2-hydroxy-1-propoxy side chain is ortho to the pyridazine ring and $R^1$ is other than hydrogen and is meta or para to the 3-alkylamino-2-hydroxy-1-propoxy side chain.

8. The pharmaceutical composition of claim 1 wherein the 3-alkylamino-2-hydroxy-1-propoxy side chain is meta or para to the pyridazine ring and $R^1$ is other than hydrogen and is ortho to the 3-alkylamino-2-hydroxy-1-propoxy side chain.

9. The pharmaceutical composition of claim 1 wherein $R^1$ is acetylamino, $R^2$ is hydrogen and the 3-alkylamino-2-hydroxy-1-propoxy side chain and the acetylamino group are in a 1,2,4- or 1,2,5-arrangement.

10. The pharmaceutical composition of claim 1 wherein the pyridazinone compound is present in an amount of from about 25 mg. to about 500 mg.

11. The method of claim 2 in which the pyridazinone compound is administered in a daily dosage of from about 100 mg. to about 2 g.

* * * * *

UNITED STATES PATENT AND TRADEMARK OFFICE
CERTIFICATE OF CORRECTION

PATENT NO. : 4,011,321

DATED : March 8, 1977

INVENTOR(S) : William John Coates, Anthony Maitland Roe and Robert Antony Slater It is certified that error appears in the above-identified patent and that said Letters Patent are hereby corrected as shown below:

On the first page of the patent, in the left-hand column, following item [62] insert the following:

[30] Foreign Application Priority Data

December 19, 1973   United Kingdom 58726

Signed and Sealed this fifth Day of July 1977

[SEAL]

Attest:

RUTH C. MASON
*Attesting Officer*

C. MARSHALL DANN
*Commissioner of Patents and Trademarks*